(12) United States Patent
Oda

(10) Patent No.: US 7,156,855 B2
(45) Date of Patent: Jan. 2, 2007

(54) INTRAOCULAR LENS INJECTION INSTRUMENT

(75) Inventor: Haruo Oda, Gamagori (JP)

(73) Assignee: Nidek Co., Ltd., Aichi (JP)

( * ) Notice: Subject to any disclaimer, the term of this patent is extended or adjusted under 35 U.S.C. 154(b) by 111 days.

(21) Appl. No.: 10/670,340

(22) Filed: Sep. 26, 2003

(65) Prior Publication Data

US 2004/0097956 A1    May 20, 2004

(30) Foreign Application Priority Data

Sep. 27, 2002    (JP)    ............................. 2002-283403

(51) Int. Cl.
*A61F 9/00*    (2006.01)
(52) U.S. Cl. .................................... 606/107
(58) Field of Classification Search ................ 606/107; 623/6.12; 604/221, 222, 229, 57, 63, 181–187, 604/208, 230, 234, 223
See application file for complete search history.

(56) References Cited

U.S. PATENT DOCUMENTS

| | | | |
|---|---|---|---|
| 4,906,247 A * | 3/1990 | Fritch ........................ | 606/107 |
| 5,437,678 A * | 8/1995 | Sorensen .................... | 606/107 |
| 5,474,562 A | 12/1995 | Orchowski et al. | |
| 5,626,601 A * | 5/1997 | Gershony et al. ........... | 606/194 |
| 5,766,181 A * | 6/1998 | Chambers et al. .......... | 606/107 |
| 5,873,879 A | 2/1999 | Figueroa et al. | |
| 5,928,245 A | 7/1999 | Wolf et al. | |
| 6,048,348 A * | 4/2000 | Chambers et al. .......... | 606/107 |
| 6,251,114 B1 * | 6/2001 | Farmer et al. ............... | 606/107 |
| 6,336,932 B1 * | 1/2002 | Figueroa et al. ............ | 606/107 |
| 6,666,871 B1 * | 12/2003 | Kikuchi et al. ............. | 606/107 |
| 2003/0139749 A1 * | 7/2003 | Kikuchi et al. ............. | 606/107 |

FOREIGN PATENT DOCUMENTS

| | | |
|---|---|---|
| EP | 0 477 466 A1 | 4/1992 |
| EP | 0 937 443 A2 | 8/1999 |
| EP | 1 332 731 A1 | 8/2003 |
| WO | WO 96/37152 A | 11/1996 |

\* cited by examiner

*Primary Examiner*—Michael J. Hayes
*Assistant Examiner*—Michael Mendoza
(74) *Attorney, Agent, or Firm*—Oliff & Berridge, PLC

(57) ABSTRACT

An intraocular lens insertion instrument includes: a cylinder (10, 20, 60) provided with an insertion part (11) which is inserted in an eye through an incision formed in the eye; a push-out unit (30) which is mounted axially movably in the cylinder to push out an intraocular lens (40) placed in the cylinder to the outside through the insertion part; and a working pressure adjustment unit (22, 23, 24; 70, 72, 80, 81) which is set in contact with the push-out unit to adjust working pressure needed to move the push-out unit by changing frictional force on the push-out unit.

7 Claims, 4 Drawing Sheets

INTRAOCULAR LENS INJECTION INSTRUMENT

BACKGROUND OF THE INVENTION

1. Field of the Invention

The present invention relates to

The present invention relates to an instrument for injecting an intraocular lens into an eye of a patient.

2. Description of Related Art

As one of operative treatments for cataract, generally used is a method of removing a crystalline lens from an eye of a patient and then injecting an intraocular lens in place of the crystalline lens. To inject the intraocular lens, the following steps are taken: first making an incision in an eyeball of a patient's eye; fragmenting and aspirating a clouded crystalline lens through the incision by for example an ultrasonic cataract-surgery device (a phaco-emulsification device); and then injecting the intraocular lens into the eye through the incision to implant it in place of the crystalline lens.

If a large incision is made, it may become a burden on the eyeball and also cause astigmatism of the patient's eye after the operation. To prevent such the disadvantages, an intraocular lens injecting instrument called an injector is used to inject a foldable intraocular lens into an eye through a smaller incision. In this injector, the foldable intraocular lens held in a housing of the injector is pushed toward the tip of the injector while being folded into a smaller shape. Thereafter, the intraocular lens is pushed out of the tip of the injector inserted in the eye through the incision and is spread (unfolded) in the eye.

Working pressure of the above injector to push out the intraocular lens (i.e., force needed to operate a push-out device) is fixed. Thus, the injector may often be hard to operate because some operators feel such fixed working pressure as too light (too low) or others feel it as too heavy (too high).

SUMMARY OF THE INVENTION

The present invention has been made in view of the above circumstances and has an object to overcome the above problems and to provide an intraocular lens injection instrument of which working pressure to push out an intraocular lens can be adjusted.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided an intraocular lens insertion instrument including: a cylinder provided with an insertion part which is inserted in an eye through an incision formed in the eye; a push-out unit which is mounted axially movably in the cylinder to push out an intraocular lens placed in the cylinder to the outside through the insertion part; and a working pressure adjustment unit which is set in contact with the push-out unit to adjust working pressure needed to move the push-out unit by changing frictional force on the push-out unit.

According to another aspect, the invention provides an intraocular lens insertion instrument including: a cylinder provided with an insertion part which is inserted in an eye through an incision formed in the eye; a shaft which is mounted axially movably in the cylinder to push out an intraocular lens placed in the cylinder to the outside through the insertion part; and an O-ring which is set in contact with the shaft and a washer which is set in contact with the O-ring, to adjust working pressure needed to move the shaft by changing frictional force on the shaft.

Furthermore, according to another aspect, the invention provides an intraocular lens insertion instrument including: a cylinder provided with an insertion part which is inserted in an eye through an incision formed in the eye; a shaft which is mounted axially movably in the cylinder to push out an intraocular lens placed in the cylinder to the outside through the insertion part; and a spring set in contact with the shaft to adjust working pressure needed to move the shaft by changing frictional force on the shaft.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

A detailed description of a preferred embodiment of an intraocular lens injection instrument embodying the present invention will now be given referring to the accompanying drawings.

Figure 1:
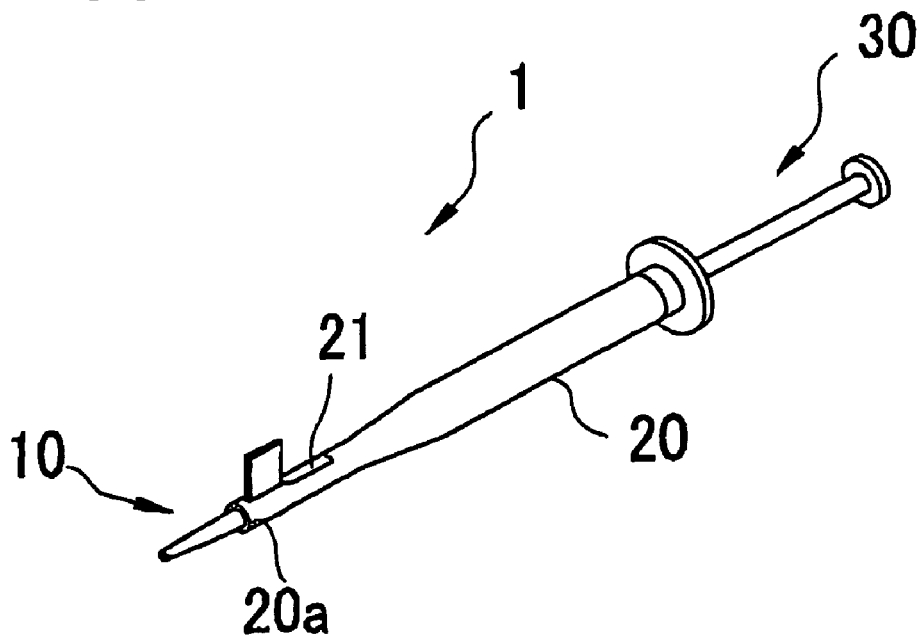
FIG. 1 is a schematic perspective view of an intraocular lens injection instrument in a first embodiment.
Figure 2:
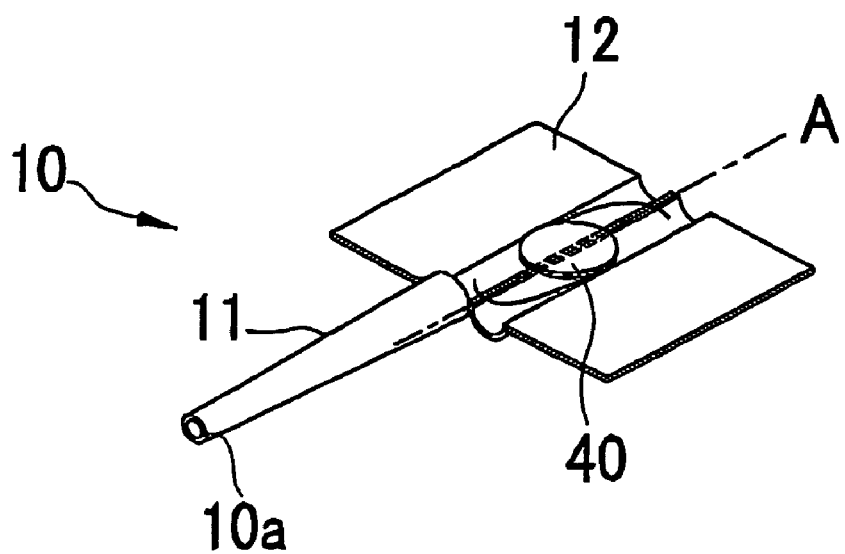
FIG. 2 is a schematic perspective view of an insertion tube.

FIG. 1 is a schematic perspective view of an intraocular lens injection instrument in the present embodiment; and FIG. 2 is a schematic perspective view of an insertion tube whose lens-placing part is opened.

Numeral 1 is a main unit of the insertion instrument, The main unit 1 includes, in order of insertion into an eye, an insertion tube 10 which holds an intraocular lens 40 and is inserted in the eye through an incision formed therein, an outer cylinder element 20 having a tip end 20a in which the insertion tube 10 is mounted, and a push-out device 30 for pushing out the intraocular lens 40 through a tip end 10a of the insertion tube 10 mounted in the outer cylinder element 20. It is to be noted that the insertion tube 10 may be united with the outer cylinder element 20.

As shown in FIG. 2, the insertion tube 10 is integrally constructed of a tapered insertion part 11 whose diameter becomes smaller toward the tip end 10a and a placing part 12 in which the intraocular lens 40 is placed in a folded state. The insertion part 11 is of a hollow cylindrical shape so that the folded intraocular lens 40 is moved through the hollow portion and discharged out through the tip end 10a. The placing part 12 is configured to be openable and closable about a dashed line A. The intraocular lens 40 is placed in the placing part 12 in an opened state and then folded when the placing part 12 is closed. The intraocular lens to be used may be any one of existing foldable intraocular lenses. The structures of the insertion part 11 and the placing part 12 are well known in the art and therefore the detailed explanations thereof are here omitted.

The outer cylinder element 20 is formed, near the tip end 20*a*, with an opening 21 for mounting therein the insertion tube 10. The insertion tube 10 with the placing part 12 closed is put and mounted in the outer cylinder element 20 through the opening 21.

Figure 3:
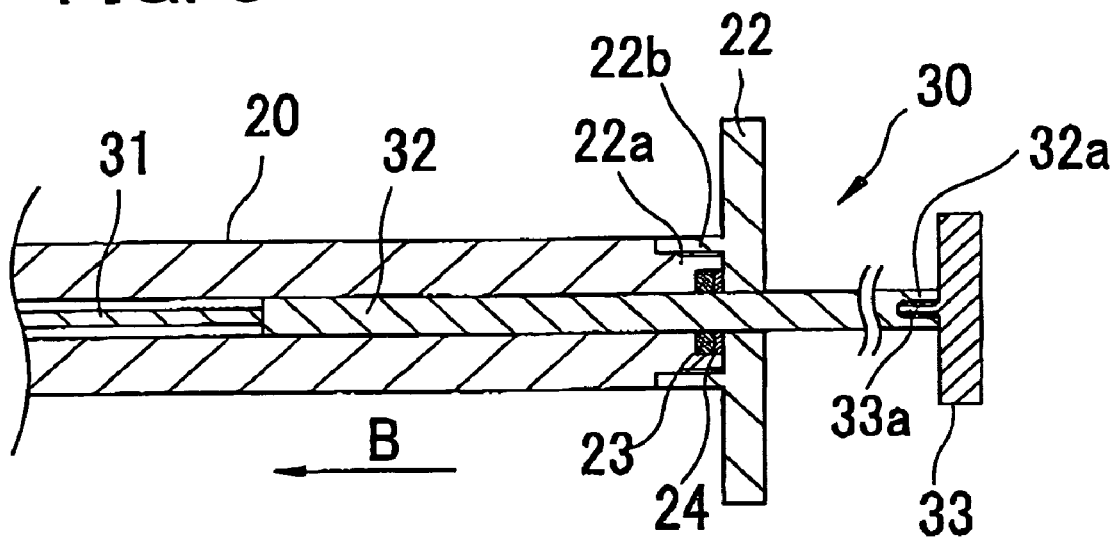
FIG. 3 is a partially sectional view schematically showing an outer cylinder element and a push-out device.

FIG. 3 is a partially sectional view schematically showing the outer cylinder element 20 in which the push-out device 30 is mounted. The outer cylinder element 20 is of a hollow cylindrical shape in which the push-out device 30 is mounted to be movable (slidable) in an axial direction of the outer cylinder element 20. The push-out device 30 is constructed of a push portion (push rod) 31, a shaft 32, and a push member 38. The push portion 31 is fixed to an end of the shaft 32 and used to push the intraocular lens 40 out through the tip end 10*a* when the shaft 32 is moved or slid frontward (in the direction of an arrow B in FIG. 8). The push member 33 is provided with a male screw 33*a* which engages with a female screw 32*a* of the shaft 32. Thus, the push member 33 is fixed to the shaft 32. By push of this push member 33 with fingers, the operator can move or slide the shaft 32 and the push portion 31 frontward.

Figure 4:
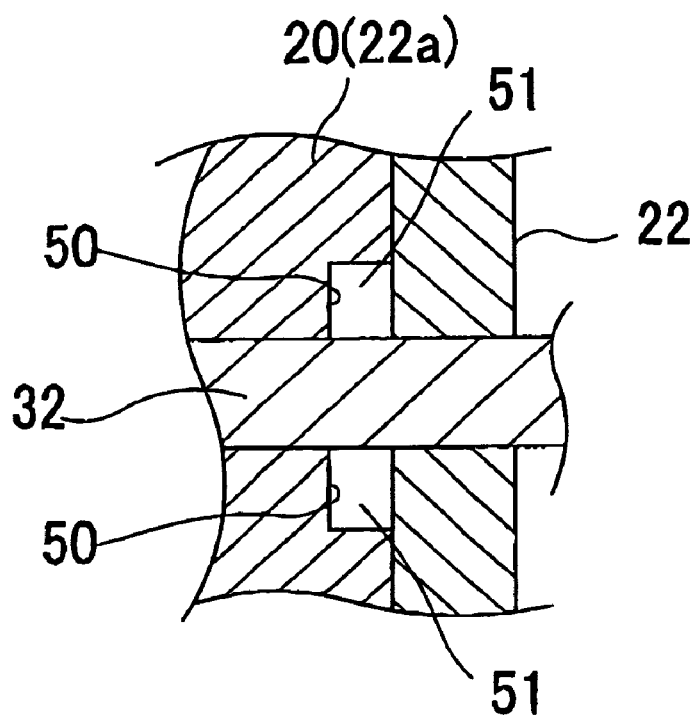
FIG. 4 is an enlarged view showing a cavity defined by the outer cylinder element and a flange.

A rear end (opposite to the tip end 20*a*) of the outer cylinder element 20 is formed with a male screw 22*a* which engages with a female screw 22*b* of a flange 22. Thus, the flange 22 is attached to the outer cylinder element 20. As shown in FIG. 4, the outer cylinder element 20 is also provided with a cylindrical recess 50 at the rear end. When the flange 22 is attached to the outer cylinder element 20, a cavity 51 is produced between the outer cylinder element 20 and the flange 22. In this cavity 51, as shown in FIG. 3, an O-ring 23 and a washer 24 which are elastic elements are set. The inner diameter of the O-ring 23 is equal to or slightly smaller than the diameter of the shaft 32 so that the inner periphery of the O-ring 32 is constantly in full contact with the shaft 32.

The O-ring 23 may be any body which is deformed under a predetermined pressure or more, for example, a rubber O-ring. Along with the O-ring 23, the washer 24 is also slid on the shaft 32 and set in the cavity 51 (the recess 50). The clearance area in the cavity 51 is changed according to the thickness of the washer 24, so that the working pressure needed to move the push-out device 30 is adjusted. It is to be noted that the total thickness of the O-ring 23 and the single washer 24 in the axial direction is determined to be slightly larger than the depth (length in the axial direction) of the cavity 51. Plural washers 24 are prepared so that the number of washers 24 to be set in the cavity 51 may be selected to provide the working pressure desired by the operator.

Figure 5A:
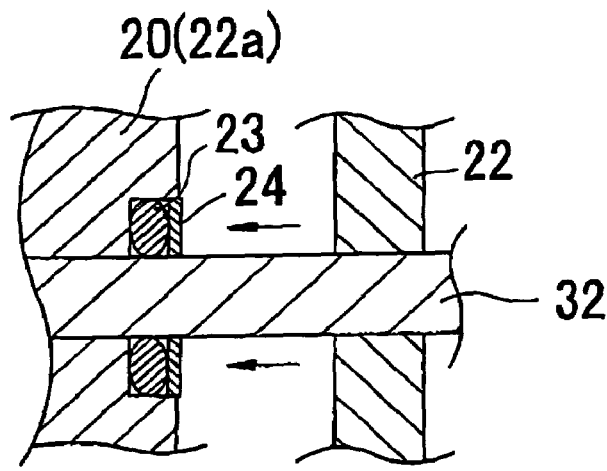
FIGS. 5A–5C are enlarged views showing a process for adjustment of working pressure.
Figure 5B:
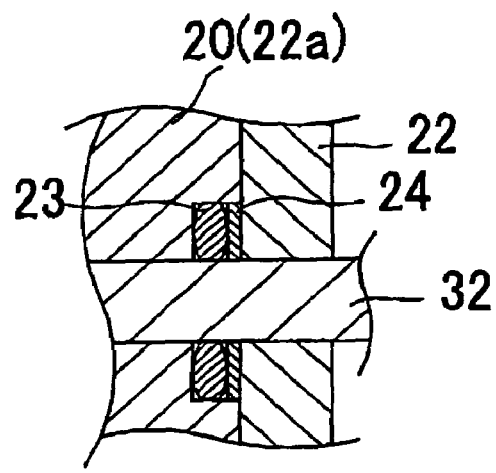

Next, explanation is made on a process of adjusting the working pressure of the above structured intraocular lens, referring to FIG. 5.

At first, the push member 33 is unscrewed from the shaft 32 and the flange 22 is detached from the outer cylinder element 20. The O-ring 32 and the washer 24 (single) are slid on the shaft 32 and set in the recess 50. In this case where the O-ring 23 and the single washer 24 are set in superimposed relation in the recess 50, the total thickness of them becomes larger than the depth (length in the axial direction) of the recess 50 as shown in FIG. 5A. When the flange 22 is then attached to the outer cylinder element 20, the flange 22 pushes the O-ring 23 through the washer 24 in the axial direction. The O-ring 23 is thus compressed in the cavity 51. This results in increases in contact area and contact pressure between the O-ring 23 and the shaft 32, raising the frictional force therebetween, thus increasing the working pressure to move the push-out device 30 in the axial direction.

Figure 5C:
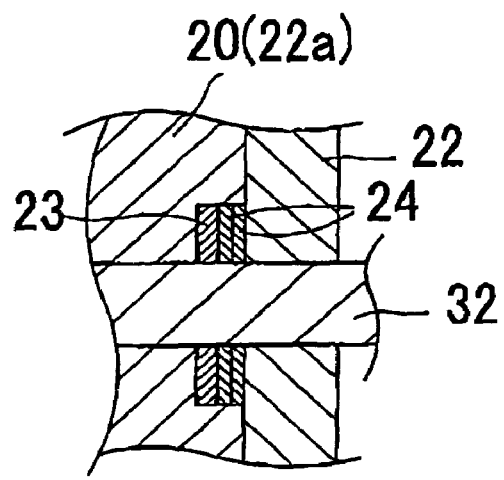

Alternatively, when two washers 24 are used at shown in FIG. 5C, the O-ring 23 is compressed into a more largely flattened state as compared with the case of using the single washer 24. This compression increases the contact pressure of the O-ring 23 with the shaft 32. Accordingly, the working pressure needed for moving the push-out device 30 in the axial direction can be increased more than that in the case of using the single washer 24. To the contrary, to reduce the working pressure, all the washers 24 have only to be removed from the cavity 51. The working pressure needed for moving the push-out device 30 in the axial direction can be adjusted by the above simple process, so that the user (operator) can appropriately determine favorable working pressure.

After the adjustment of the working pressure, the insertion tube 10 in which the intraocular lens 40 is placed is mounted in the outer cylinder element 20. The push-out device 30 is then moved or slid in the axial direction under the desired working pressure, pushing the intraocular lens 40 to the outside (namely, into the eye).

It is to be noted that the above embodiment is explained using the foldable intraocular lens; alternatively, a hard type intraocular lens which can not be folded may be used. In this case, the present invention is adapted to an insertion instrument for inserting the hard type intraocular lens.

Figure 6:
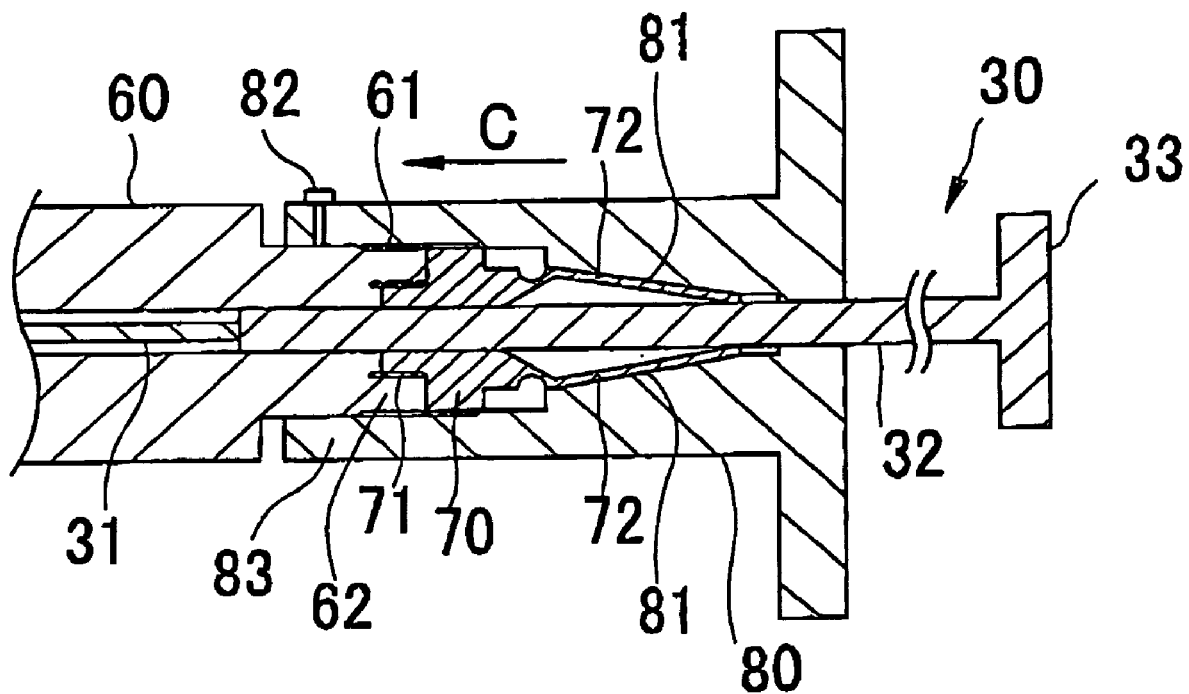
FIG. 6 is a partially sectional view of an intraocular lens injection instrument in another embodiment.

Next, a second embodiment of the present invention is explained below with reference to FIG. 6. In this embodiment, the elements or parts having the same functions as those in the first embodiment are indicated with the same numerals and their explanations are omitted.

Numeral 60 is an outer cylinder element whose rear end (an opposite end to a tip end) is formed with a male screw 61 which engages with a female screw 83 of a flange 80. Numeral 70 is a working pressure adjusting member formed with a central hole in which the push-out device 30 is inserted. The working pressure adjusting member 70 is also formed, at the front side (which contacts with the outer cylinder element 60), with a male screw 71 which engages with a female screw 62 provided in the rear portion of the outer cylinder element 60. The working pressure adjusting member 70 is provided, at the rear side, with a tapered plate spring 72 with slits. The inside of the flange 80 is formed with a tapered wall surface 81 which axially presses the plate spring 72 to the shaft 32. It is to be noted that when the plate spring 72 is not pressed by the wall surface 81, the tip end of the plate spring 72 is in noncontact with the shaft 32 or into contact with the same with small contact area and contact pressure. Numeral 82 is a screw for fastening the flange 80 to the outer cylinder element 60. In the present embodiment, three screws 82 are arranged at equal intervals on the outer periphery of the flange 80 to securely attach the flange 80 to the outer cylinder element 60.

To assemble the above instrument, the working pressure adjustment member 70 is attached to (screwed in) the outer cylinder element 60, the push-out device 30 is mounted in the hollow portion of the outer cylinder element 60, and then the flange 80 is turned to engage a female screw 83 thereof with the male screw 61 of the outer cylinder element 60. At this time, as the flange 80 is screwed moving frontward (in the direction of an arrow C in FIG. 6), the wall surface 81 of the flange 80 should axially press the plate spring 72.

When pressed by the wall surface 81 of the flange 80, the plate spring 72 is bent to come into contact with the shaft 32, increasing the contact area and contact pressure. Thus, the working pressure of the push-out device 30 can be increased When the desired working pressure of the push-out device 30 is produced, the screw 82 is tightened to securely fasten the flange 80 to the outer cylinder element 60. To reduce the working pressure, on the other hand, the screw is loosened and the flange 80 is turned moving backward (in the opposite direction to the arrow C in FIG. 6). In the above manner, the working pressure of the push-out device 30 can simply be adjusted according to the axially moving amount of the flange 80.

According to the present invention, as explained above, the working pressure of the intraocular lens insertion instrument to inject the intraocular lens into the eye can appropriately be adjusted to favorable working pressure according individual users (operators).

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. An intraocular lens insertion instrument including:
   a cylinder provided with an insertion part which is inserted in an eye through an incision formed in the eye;
   a push-out unit which is mounted axially movably in the cylinder to push out an intraocular lens placed in the cylinder to the outside through the insertion part;
   an elastic member which is set in contact with the push-out unit and deformed under pressure; and
   an adjustment member which is set to push out the elastic member in an axial direction of the push-out unit to change a deformed state of the elastic member, and the adjustment member being adapted to adjust working pressure need to move the push-out unit by changing frictional force on the push-out unit according to the deformed state of the elastic member, wherein the adjustment member includes a washer.

2. The intraocular lens insertion instrument according to claim 1, wherein the elastic member includes an O-ring.

3. The intraocular lens insertion instrument according to claim 1, wherein the push-out unit includes a shaft.

4. An intraocular lens insertion instrument including:
   a cylinder provided with an insertion part which is inserted in an eye through an incision formed in the eye;
   a shaft which is mounted axially movably in the cylinder to push out an intraocular lens placed in the cylinder to the outside through the insertion part; an O-ring which is set in contact with the shaft; and
   an adjustment member which is set to push out the O-ring in an axial direction of the shaft to change a deformed state of the O-ring, and the adjustment member being adapted to adjust working pressure need to move the shaft by changing frictional force on the shaft according to the deformed state of the O-ring.

5. The intraocular lens insertion instrument according to claim 4, wherein the adjustment member includes a washer.

6. An intraocular lens insertion instrument including:
   a cylinder provided with an insertion part which is inserted in an eye through an incision formed in the eye;
   a push-out unit which is mounted axially movably in the cylinder to push out an intraocular lens placed in the cylinder to the outside through the insertion part; and
   a plate spring which is set in contact with the push-out unit to adjust working pressure needed to move the push-out unit by changing frictional force on the push-out unit.

7. The intraocular lens insertion instrument according to claim 6, wherein the push-out unit includes a shaft.

* * * * *